United States Patent [19]
Kim et al.

[11] Patent Number: 5,952,494
[45] Date of Patent: Sep. 14, 1999

[54] METHOD FOR THE PREPARATION OF PYRIDO BENZOXAZINE DERIVATIVES

[76] Inventors: Youseung Kim, 456, Hyundai Apt. 74-505, Apkujong-Dong, Kangnam-ku; Soon Bang Kang, 175-59, Jungkok 3-Dong, Sungdong-ku; Seonhee Park, Jukong Apt. 403-606, Sankye 7-Dong, Nowon-ku, all of Rep. of Korea

[21] Appl. No.: 08/443,884

[22] Filed: May 26, 1995

[30] Foreign Application Priority Data

May 28, 1994 [KR] Rep. of Korea ............ 94-11749

[51] Int. Cl.$^6$ ............................................ C07D 498/06
[52] U.S. Cl. .............................................. 544/101
[58] Field of Search ............................................ 544/101

[56] References Cited

U.S. PATENT DOCUMENTS

| | | | |
|---|---|---|---|
| 5,516,926 | 5/1996 | Kim et al. | 556/418 |
| 5,516,927 | 5/1996 | Kim et al. | 556/418 |
| 5,539,110 | 7/1996 | Kim et al. | 544/101 |

FOREIGN PATENT DOCUMENTS

| | | |
|---|---|---|
| 84-2141 | 8/1981 | Rep. of Korea. |
| 93-4309 | 8/1991 | Rep. of Korea. |
| 93-4310 | 8/1991 | Rep. of Korea. |
| 93-10027 | 11/1991 | Rep. of Korea. |
| 93-10041 | 11/1991 | Rep. of Korea. |
| 93-12787 | 12/1991 | Rep. of Korea. |

OTHER PUBLICATIONS

Bouzard, Chemical Abstract 110:57479 (1988).
Bouzard, Tetrahedron Letters, 29(16), pp. 1931–1934 (1988).
Egawa, Hiroshi, et al. (1986) "A New synthesis of 7H–Pyridol[1,2,3–de][1,4]benzoaxazine Derivatives Including an Antibacterial Agent, Ofloxacin", *Chem. Pharm. Bull* 34 (10):4098–4102.

*Primary Examiner*—Philip I. Datlow

[57] ABSTRACT

There is disclosed a method for the preparation of pyrido benzoxazine derivative having the following formula I, that is improved in both production coat and yield.

The method comprises reacting a compound of the following general formula II with tetraalkyl ammonium fluoride or with a mixture of tetraalkyl ammonium halide and metal fluoride in an organic solvent at a reaction temperature of about 30 to about 100° C. for 1 to 3 hours under stirring; and reacting the resulting solution with a metal hydroxide or a metal carboxylate dissolved in water or in a mixture of water and alcohol, for 1 to 3 hours under heat.

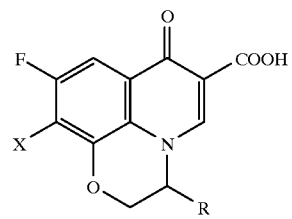

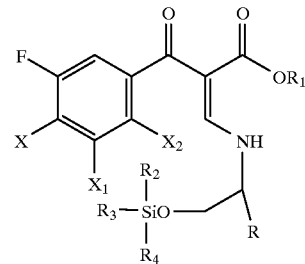

wherein X is a fluorine or chlorine atom and $X_1$ and $X_2$ each is a halogen atom or a nitro group, R is an alkyl group containing 1 to 4 carbon atoms and $R_1$, $R_2$, $R_3$ and $R_4$ each is an alkyd group or allyl group containing 1 to 8 carbon atoms.

6 Claims, No Drawings

METHOD FOR THE PREPARATION OF PYRIDO BENZOXAZINE DERIVATIVES

BACKGROUND OF THE INVENTION

1. Field of the Invention

The present invention relate to an advanced method for the preparation of pyrido benzoxazine derivatives and pharmaceutically acceptable salts, antibacterially active compounds and, more particularly, to an improvement in production cost and production yield along with the novel method.

2. Description of the Prior Art

According to literature (Chem. Pharm. Bull., 32, pp 4907–4913 (1984)), it is reported that the pyrido benzoxazine derivatives which are represented by the following general formula I are very antibacterially active compounds and have potent sterilization power for a wide range of bacteria:

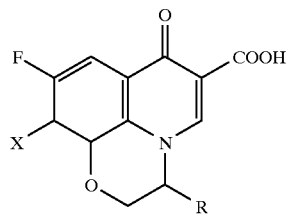

I wherein X is a fluorine atom or chlorine atom and R is an alkyl group containing 1 to 4 carbon atoms.

Preparation methods for the antibacterially active compound of the formula I are disclosed in many patents, for example, Korean Patent Publication No. 84-2141 and Korean Patent Laid-Open Publication Nos. 92-22050, 93-4309, 93-4310, 93-10027, 93-10041 and 93-12787.

Those conventional methods, however, are disadvantageous in many aspects. For example, the reaction procedure employed in the conventional methods is carried out in even 8 steps using 2,3,4-trifluoronitrobenzene as a starting material, so that production yield is low. Further, since the conventional methods use Raney Nickel, which is dangerous due to strong flammability, it is unsuitable to industrial mass production.

SUMMARY OF THE INVENTION

It is, therefore, an object of the present invention to provide a novel method for the preparation of pyrido benzoxazine derivatives and pharmaceutically acceptable salts thereof, shortened in procedure steps.

It Is another object of the present invention to provide a novel method for the preparation of pyrido benzoxazine derivatives and pharmaceutically acceptable salts thereof, improved in production yield.

It is a further object of the present invention to provide a novel method for the preparation of pyrido benzoxazine derivatives and pharmaceutically acceptable salts thereof, suitable to mass production.

In accordance with the present invention, the above objects could be accomplished by a provision of a method for the preparation of pyrido benzoxazine carboxylic acid derivative having the following general formula I:

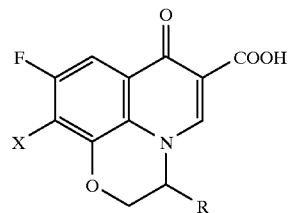

I wherein X is a fluorine or chlorine atom and R is an alkyl group containing 1 to 4 carbon atoms, comprising the steps of: reacting a compound of the following general formula II:

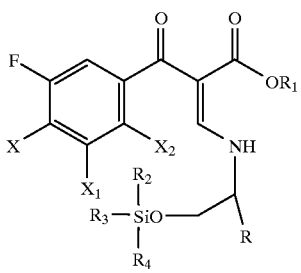

II wherein X is as defined above, $X_1$ and $X_2$ each is a halogen atom or a nitro group, R is as defined above, and $R_1$, $R_2$, $R_3$ and $R_4$ each is an alkyl group or allyl group containing 1 to 8 carbon atoms, with tetraalkyl ammonium fluoride or with a mixture of tetraalkyl ammonium halide and metal fluoride in an organic solvent at a reaction temperature of about 30 to about 100° C. for 1 to 3 hours under stirring; and reacting the resulting solution with a metal hydroxide or a metal carbonate dissolved in water or in a mixture of water and alcohol, for 1 to 3 hours under heat.

These and other objects and advantages of the present invention will become more apparent as the following description proceeds.

DETAILED DESCRIPTION OF THE INVENTION

In accordance with the present invention, pyrido benzoxazine derivatives of formula I, antibacterially active compounds, can be prepared from a compound represented by the formula II, a novel compound.

The novel compound of formula II, starting material for the antibacterially active compound, is in detail described in Korean Patent Application No. 11747/94 to the present inventors, filed on May 28, 1994, corresponding to U.S. Pat. No. 5,516,927 issue May 14, 1996 along with its preparation method. This compound can be prepared from an acrylate derivative through two steps according to the just mentioned application.

In accordance with the present invention, the pyrido benzoxazine derivative of formula I is prepared by reacting a compound of formula II with tetraalkyl ammonium fluoride or with a mixture of tetraalkyl ammonium halide and metal fluoride in an organic solvent at a reaction temperature of about 30 to about 100° C. for 1 to 3 hours under stirring, and reacting the resulting solution with a base dissolved in water or in a mixture of water and alcohol for 1 to 3 hours under heat.

As an organic solvent suitable for the reaction of the compound of formula II, there may be used tetrahydrofuran, acetonitrile, or dimethylform amide.

Tetraalkyl ammonium fluoride useful in the present invention includes tetramethyl ammonium fluoride, tetraethyl ammonium fluoride, and tetrabutyl ammonium fluoride.

With regard to tetraalkyl ammonium halide, preferred is tetramethyl ammonium chloride, tetramethyl ammonium bromide, tetramethyl ammonium iodide, tetraethyl ammonium chloride, tetraethyl ammonium bromide, tetraethyl ammonium iodide, tetrapropyl ammonium bromide, tetrapropyl ammonium iodide, tetrabutyl ammonium chloride, tetrabutyl ammonium bromide, tetrabutyl ammonium iodide, tetrapentyl ammonium bromide, and tetrapentyl ammonium iodide.

For the tetrapentyl ammonium iodine usable in the present invention, it is selected from a group consisting of cesium fluoride, potassium fluoride, calcium fluoride and sodium fluoride.

It Is preferred that the equivalent ratio of the compound of formula II to tetraalkyl ammonium fluoride is in a range of 2 to 4. In case of reaction with a mixture of tetraalkyl ammonium halide and metal fluoride, the compound of formula II preferably has equivalent ratios to tetraalkyl ammonium halide ranging from 2 to 4 under the condition that the equivalent ratio of tetraalkyl ammonium halide to metal fluoride is 2.

Base suitable to react with the novel compound of formula II may be selected from a group consisting of metal hydroxides and metal carbonates. Preferred metal hydroxides include calcium hydroxide, sodium hydroxide, potassium hydroxide and lithium hydroxide. Preferred metal carbonates include potassium carbonate, sodium carbonate, lithium carbonate and barium carbonate, and said metal carbonate is selected from a group consisting of potassium carbonate, sodium carbonate, lithium cabornate and barium carbonate.

When the novel compound of formula II is reacted with the base, that is, metal hydroxide or metal carbonate, the equivalent ratio is preferably in a range of from 2 to 4.

For the reaction with compound of formula II, the base is dissolved in water or a mixture of water and alcohol. In case of the mixture, water is mixed with alcohol in a volume ratio of 2:1 to 3:1.

As described hereinbefore, the antibacterially active compounds of formula I can be prepared in simple and with ease, according to the present invention, which results in high production yield. Consequently, the method of the present invention can complete a first cyclic reaction, deprotection, a second cyclic reaction and hydrolysis in one reactor and thus, is very advanced and economical as compared with the conventional methods having complicate multi-reaction steps and unsuitable to application of industrialization.

Of cause, the prepared compound of formula I may be reacted with an organic acid such as methane sulfonic acid and p-toluene sulfonic acid or an inorganic acid such as hydrochloric acid and sulfuric acid, so as to produce an acid addition salt. Also, it may be reacted with sodium or potassium, to give a corresponding carboxylic acid salt.

Products obtained by the method of the present invention may be separated and filtered in a conventional manner such as evaporation, filtration, extraction, re-crystallization and the combination thereof.

The preferred embodiments of the present invention will now be further described with reference to specific examples. Unless otherwise stated all percentage, part and ratio therein are by weight.

EXAMPLE 1

Preparation of 9,10-difluoro-2,3-dihydro-3-methyl-7-oxo-7H-pyrido [1,2,3-de][1,4]-benzoxazine-6-carboxylic acid (I: X=fluoro, R=methyl)

220 mg (0.447 mmol) of ethyl 2-(2-nitro-3,4,5-trifluoro)benzoyl-3-(1-t-butyldimethylsilyloxyprop-2-ylamino) acrylate (II: X, $X_1$=fluoro, $X_2$=nitro, R=methyl, $R_1$=ethyl, $R_2,R_3$=methyl, $R_4$=t-butyl) was added to 10 ml of tetrahydrofuran and cooled to 0° C. To this solution, 0.41 g (1.56 mmol) of tetrabutyl ammonium fluoride dissolved in tetrahydrofuran was added dropwise, and stirred for 30 min. and refluxed under heat for another 30 min. Thereafter, 2 ml of 10% potassium hydroxide aqueous solution was added and refluxed under heat for 30 min. After being cooled to room temperature, the reaction mixture was filtered to remove unsolved substance. The filtered liquid was removed under reduced pressure (25° C./10 mmHg) and 20 ml of water was added to the residue left. The resulting aqueous solution was washed with 5 ml of chloroform once and then, 1 N hydrochloric acid solution was slowly added, to adjust pH of the aqueous solution into 3. Filtration was carried out to obtain a solid which was, in turn, washed with 5 ml of water and 5 ml of a mixture solution of ethanol and ethyl other (volume ratio 1:4), respectively and then, dried, to give 108 mg of the object solid product (yield 86%).

m.p.: 308° C. (dec.); NMR(TFA-$d_1$) ppm: 9.39(1H, s), 8.10(1H, dd, J=10.8H), 5.11–5.26(1H, m), 4.79(1H, dd, J=2.12H), 4.65(1H, dd, J=2.12H), 1.82(3H, d, J=6.7H).

EXAMPLE 2

Preparation of 9,10-difluoro-2,3-dihydro-3-methyl-7-oxo-7H-pyrido[1,2,3-de][1,4]-benzoxazine-6-carboxylic acid (I: X=fluoro, R=methyl)

202 mg (0.436 mmol) of ethyl 2-(2,3,4,5-tetrafluoro) benzoyl-3-(1-t-butyldimethylsilyloxy-prop-2-ylamino) acrylate (II: X, $X_1$, $X_2$=fluoro, R=methyl, $R_1$-ethyl, $R_2$, $R_3$m=ethyl, $R_4$=t-butyl) was added to 10 ml of tetrahydrofuran and cooled to 0° C. This reaction mixture was treated in the same manner as that of Example 1, to give 104 mg of the object solid product (yield 85%).

m.p.: >300° C.

EXAMPLE 3

Preparation of 9,10-difluoro-2,3-dihydro-3-methyl-7-oxo-7H-pyrido[1,2,3-de][1,4]-bensoxazine-6-carboxylic acid (I: X=fluoro, R=methyl)

1.0 g (2 mmol) of ethyl 2-(2-nitro-3,4,5-trifluoro)benzoyl-3-(1-t-butyldimethylsilyloxyprop-2-ylamino)acrylate (II: X, $X_1$=fluoro, $X_2$=nitro, R=methyl, $R_1$-ethyl, R2, $R_3$=ethyl, $R_4$=t-butyl) was added to 10 ml of tetrahydrofuran. To this solution, 5.5 ml (5.5 mmol) of 1.0 M tetrahydrofuran solution containing tetrabutyl ammonium fluoride was added dropwise, and stirred for 90 min. After being cooled to room temperature, the reaction mixture was filtered to remove unsolved substance. The filtered liquid was removed under reduced pressure (25° C./10 mmHg). Residue was added with 15 ml of ethanol, 10 ml of water and 1.1 g (8 mmol) of potassium carbonate and then stirred under heat for 2 hours. The solvent was removed under reduced pressure (25° C./10 mmHg), and 20 ml of water was added to residue left. Precipitate was filtered off and tho filtered liquid was allowed to have pH 3 by adding 1 N hydrochloric acid solution. Filtration was carried out to obtain a solid which was, in turn, washed with 5 ml of water and 5 ml of a mixture solution of ethanol and ethyl other (volume ratio 1:4), respectively and then, dried, to give 0.49 g of the object solid product (yield 86%).

m.p.: >300° C.

EXAMPLE 4

Preparation of 9,10-difluoro-2,3-dihydro-3-methyl-7-oxo-7H-pyrido [,1,2,3-de][1,4]-benzoxazine-6-carboxylic acid (I: X=fluoro, R=methyl)

Ethyl 2-(2,3,4,5-tetrafluoro) benzoyl-3-[1-t-butyldimethylsilyloxyprop-2-ylamino)acrylate (II. X, $X_1$, $X_2$=fluoro, R=methyl, $R_1$=ethyl, $R_2$, $R_3$=-ethyl, $R_4$=t-butyl) was treated in the same manner as that of Example 3, to give the object solid product (yield 88%).

m.p.: >300° C.

EXAMPLE 5

Preparation of 9,10-difluoro-2,3-dihydro-3-methyl-7-oxo-7H-pyrido [1,2,3-de][1,4]-benzoxazine-6-carboxylic acid (I: X=fluoro, R=methyl)

1.20 g (2.45 mmol) of ethyl 2-(2-nitro-3,4,5-trifluoro) benzoyl-3-(1-t-butyldimethylsilyloxyprop-2-ylamino) acrylate (II: X, $X_1$=fluoro, $X_2$=nitro, R=methyl, $R_1$=ethyl, $R_2$,R3=-ethyl, $R_4$=t-butyl) was added to 10 ml of tetrahydrofuran. To this solution, 1.36 y (4.9 mmol) of tetrabutyl ammonium chloride hydrate and 690 mg (7.35b mmol) of potassium fluoride hydrate was added and stirred under heat for 3 hours. This reactant solution was mixed with 5 ml of 10% potassium hydroxide aqueous solution and refluxed under heat for 1 hour. After being cooled to room temperature, the reaction mixture was filtered to remove unsolved substance. The filtered liquid was removed under reduced pressure (25° C./10 mmHg). Residue was added with 30 ml of water. The resulting aqueous solution was washed with 5 ml of chloroform once and then, 1 N hydrochloric acid solution was slowly added, to adjust pH of the aqueous solution into 3. Filtration was carried out to obtain a solid which was, in turn, washed with 5 ml of water and 5 ml of a mixture solution of ethanol and ethyl ether (volume ratio 1:4), respectively and then, dried, to give 578 mg of the object solid product (yield 84%).

m.p.: >300° C.

Other features, advantages and ambodiments of the invention disclosed herein will be readily apparent to those exercising ordinary skill after reading the foregoing disclosures. In this regard, while specific embodiments of the invention have been described in considerable detail, variations and modifications of these embodiments can be effected without departing from the spirit and scope at the invention as described and claimed.

What is claimed is:

1. A method for the preparation of pyrido benzoxazine carboxylic acid derivative having the following formula I:

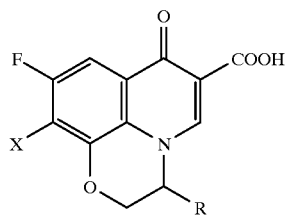

wherein X is a fluorine or chlorine atom and R is an alkyl group containing 1 to 4 carbon atoms, comprising the steps of:

reacting a compound of the following formula II:

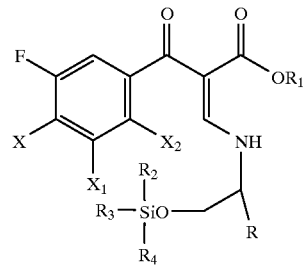

wherein X is as defined above,
$X_1$ and $X_2$ each is a halogen atom or a nitro group,
R is as defined above, and
$R_1$, $R_2$, $R_3$ and $R_4$ each is an alkyl group or allyl group containing 1 to 8 carbon atoms, with tetraalkyl ammonium fluoride or with a mixture of tetraalkyl ammonium halide and metal fluoride in an organic solvent at a reaction temperature of about 30 to about 100° C. for 1 to 3 hours under stirring; and without isolation of the intermediate produced,
reacting the resulting solution with a metal hydroxide or a metal carbonate dissolved in water or in a mixture of water and alcohol, for 1 to 3 hours under heat.

2. A method for the preparation of pyrido benzoxazine carboxylic acid derivative set forth as claim 1, wherein said organic solvent is selected from a group consisting of tetrahydrofuran, acetonitrile, pyridine, dimethylformamide and dioxane.

3. A method for the preparation of pyrido benzoxazine carboxylic acid derivative set forth as claim 1, wherein said tetraalkyl ammonium fluoride is selected from a group consisting of tetramethyl ammonium fluoride, tetraethyl ammonium fluoride, and tetrabutyl ammonium fluoride.

4. A method for the preparation of pyrido benzoxazine carboxylic acid derivative set forth as claim 1, wherein said tetraalkyl ammonium halide is selected from a group consisting of tetramethyl ammonium chloride, tetramethyl ammonium bromide, tetramethyl ammonium iodide, tetraethyl ammonium chloride, tetraethyl ammonium bromide, tetraethyl ammonium iodide, tetrapropyl ammonium chloride, tetrabutyl ammonium bromide, tetrabutyl ammonium iodide, tetrapentyl ammonium bromide, and tetrapentyl ammonium iodide.

5. A method for the preparation of pyrido benzoxazine carboxylic acid derivative set forth as claim 1, wherein said metal fluoride is selected from a group consisting of cesium fluoride, potassium fluoride, calcium fluoride and sodium fluoride.

6. A method for the preparation of pyrido benzoxazine carboxylic acid derivative set forth as claim 1, wherein said metal hydroxide is selected from a group consisting of calcium hydroxide, sodium hydroxide, potassium hydroxide and lithium hydroxide, and said metal carbonate is selected from a group consisting of potassium carbonate, sodium carbonate, lithium carbonate and barium carbonate.

* * * * *